(12) United States Patent
Brunner et al.

(10) Patent No.: US 10,357,208 B2
(45) Date of Patent: Jul. 23, 2019

(54) METHOD FOR DETERMINING A THREE-DIMENSIONAL IMAGE DATASET BY AN X-RAY DEVICE

(71) Applicants: Thomas Brunner, Nürnberg (DE); Bernd Schreiber, Forchheim (DE)

(72) Inventors: Thomas Brunner, Nürnberg (DE); Bernd Schreiber, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/726,565

(22) Filed: Oct. 6, 2017

(65) Prior Publication Data
US 2018/0098740 A1    Apr. 12, 2018

(30) Foreign Application Priority Data
Oct. 11, 2016   (DE) .................. 10 2016 219 694

(51) Int. Cl.
*G06K 9/00*   (2006.01)
*A61B 5/00*   (2006.01)
(Continued)

(52) U.S. Cl.
CPC .............. *A61B 5/7425* (2013.01); *A61B 6/03* (2013.01); *A61B 6/52* (2013.01); *A61B 6/5205* (2013.01);
(Continued)

(58) Field of Classification Search
CPC combination set(s) only.
See application file for complete search history.

(56) References Cited

U.S. PATENT DOCUMENTS

| 6,219,441 B1 | 4/2001 | Hu |
| 6,466,645 B1 | 10/2002 | Hsieh et al. |

(Continued)

OTHER PUBLICATIONS

German Office Action for German Application No. 10 2016 219 694.4 dated Jan. 26, 2018.
(Continued)

*Primary Examiner* — Alex Kok S Liew
(74) *Attorney, Agent, or Firm* — Lempia Summerfield Katz LLC (57) ABSTRACT

A method for determining a three-dimensional image dataset by an X-ray device is disclosed herein. The method includes recording projection images of an examination object from a plurality of recording angles, and reconstructing the image dataset from the projection images, wherein, for at least one examined projection image, in each case an interference condition is evaluated the fulfillment of which is dependent upon at least parts of the image data of the (respective) examined projection image and/or upon at least one parameter of the radiation source during the recording of the (respective) examined projection image and indicates that the (respective) examined projection image is a projection image with interference during the recording of which arcing has occurred in the radiation source. The method also includes disregarding at least one projection image with interference, or giving the projection image a lower weighting than all the projection images with no interference, or replacing the projection image with a synthetic projection image.

18 Claims, 4 Drawing Sheets

(51) Int. Cl.
*A61B 6/00* (2006.01)
*G06F 19/00* (2018.01)
*G06T 11/00* (2006.01)
*A61B 6/03* (2006.01)

(52) U.S. Cl.
CPC .......... *A61B 6/5264* (2013.01); *G06F 19/321* (2013.01); *G06T 11/003* (2013.01); *A61B 5/0062* (2013.01); *A61B 6/4441* (2013.01); *A61B 6/501* (2013.01)

(56) References Cited

U.S. PATENT DOCUMENTS

| | | | |
|---|---|---|---|
| 6,618,466 B1 * | 9/2003 | Ning | A61B 6/032 378/62 |
| 7,114,850 B2 | 10/2006 | Dong et al. | |
| 2004/0264629 A1 * | 12/2004 | Tang | A61B 6/032 378/7 |
| 2005/0047551 A1 | 3/2005 | Dong et al. | |
| 2006/0062443 A1 | 3/2006 | Basu et al. | |

OTHER PUBLICATIONS

Rajwade, Jaisingh. "Partial-Data Interpolation During Arcing of an X-Ray Tube in a Computed Tomography Scanner" Diss. Cleveland State University, 2011.

* cited by examiner

METHOD FOR DETERMINING A THREE-DIMENSIONAL IMAGE DATASET BY AN X-RAY DEVICE

The application claims the benefit of German Patent Application No. DE 10 2016 219 694.4, filed Oct. 11, 2016, which is hereby incorporated by reference in its entirety.

TECHNICAL FIELD

The disclosure relates to a method for determining a three-dimensional image dataset by an X-ray device, wherein projection images of an examination object are recorded from a plurality of recording angles, the image data of which describe acquired radiation intensities or attenuations determined therefrom of X-rays emitted by a radiation source of the X-ray device for a plurality of pixels, after which the image dataset is reconstructed from the projection images. The disclosure also relates to an X-ray device, a computer program, and an electronically readable data medium.

BACKGROUND

It is known to use a plurality of projection images recorded by an X-ray device in order to reconstruct a three-dimensional image dataset therefrom. This approach is used, for example, in computed tomography scans in which a radiation source and a radiation detector may be rotated about an examination object by a gantry in order to record the object from a plurality of recording angles. Also used, in particular, in the field of medical imaging, are C-arm X-ray devices with which the X-ray detector and the X-ray source are supported by a C-shaped carrier, which may be rotated and/or moved in order to change a recording perspective.

For the provision of X-rays, an X-ray tube may be used as a radiation source. In such cases, it is possible that transient arcing will occur in the X-ray tube thus causing the X-ray tube to be short-circuited for a brief period. During this short circuit, there is a temporary break in the intensity of the X-rays provided. With a two-dimensional X-ray recording, this may result in underexposure of the recording. Where three-dimensional image datasets are to be generated from a plurality of projection images, this arcing is particularly problematic for two reasons. On the one hand, in this case, a plurality of projection images is recorded with relatively short exposure times. This increases the probability of arcing occurring in the context of the data acquisition and the influence of such arcing on the individual projection image is relatively strong. On the other hand, the data from the projection images is combined in the context of the reconstruction of the three-dimensional image dataset. Consequently, the overexposure or underexposure of individual projection images results not in a homogenous change in contrast affecting the whole dataset, but potentially in banding, e.g., contrast variations within the image dataset. These may significantly complicate the interpretation of the image dataset.

SUMMARY AND DESCRIPTION

The object underlying the disclosure is accordingly to reduce image artifacts due to arcing in three-dimensional image datasets acquired by an X-ray device.

The scope of the present disclosure is defined solely by the appended claims and is not affected to any degree by the statements within this description. The present embodiments may obviate one or more of the drawbacks or limitations in the related art.

The object is achieved by a method of the type named in the introduction, wherein, for one examined projection image or several examined projection images, in each case an interference condition is evaluated the fulfillment of which is dependent upon at least parts of the image data of the (respective) examined projection image and/or upon at least one parameter of the radiation source during the recording of the (respective) examined projection image and indicates that the (respective) examined projection image is a projection image with interference during the recording of which arcing has occurred in the radiation source after which either the projection image with interference or the projection images with interference is or are disregarded during the determination of the image dataset or it is/they are given a lower weighting than all the projection images with no interference for which the interference condition is not fulfilled or it is/they are replaced by a respective synthetic projection image that is generated as a function of at least parts of the image data of the (respective) projection image with interference and at least another one of the projection images.

Hence, it is proposed that a check be performed as to whether the image data or the parameters of the radiation source during the recording of a projection image indicate that arcing has occurred in the radiation source during the recording of this projection image. In such a case, it is necessary to reduce the resulting artifacts. In the method, this may be achieved in that such a projection image with interference is disregarded or given a lower weighting in the context of the reconstruction. Alternatively, corresponding artifacts may be reduced in that, instead of the projection image with interference, a synthetic projection image is used that is dependent upon both the projection image with interference and at least another one of the projection images. As will be explained in detail below, this is possible in the context of an iterative reconstruction with which, first, an auxiliary dataset is reconstructed taking account of the projection images with interference, after which the projection images with interference are replaced by synthetic projection images obtained from this auxiliary dataset during the final reconstruction.

The method enables artifacts induced by arcing during the recording of at least one of the projection images to be significantly reduced and, under certain circumstances, completely eliminated. In particular, the formation of banding-type interference may be reduced or prevented which may greatly simplify the evaluation of the image dataset.

In the method, the interference condition may be evaluated for each of the projection images. However, it is also possible for it only to be evaluated for a subgroup of the projection images. The X-ray device may be a C-arm X-ray device or a computed tomography scanner.

Reconstruction methods for the reconstruction of the three-dimensional image dataset from the projection images may be based on the fact that, for each pixel or for groups of pixels of the projection images, in each case attenuation of the X-rays emitted by the radiation source caused by the examination object or further objects located in the beam is determined. This attenuation is dependent upon a ratio of the emitted intensity $I_0$ to the acquired intensity $I$. The emitted intensity $I_0$ may be acquired by a separate detector as is, for example, the case with computed tomography scanners. However, it is also possible to estimate this value in that electrical parameters of the radiation source and/or acquired intensities of pixels are evaluated for which it is expected that no object is located in the beam path. The attenuation may be determined on a logarithmic scale and, for example, be determined as the logarithm of the ratio of $I_0$ to I. This representation is advantageous in the context of the reconstruction because attenuation described in this way may be considered to be a line integral over a differential attenuation along the path of the X-rays. Thus, the attenuations for the individual pixels may be considered to be the Radon transform of the three-dimensional image dataset. This procedure is known from the prior art and does not require detailed explanation.

The method is particularly simple to implement if the radiation source itself identifies arcing. Then, corresponding information may be provided via a separate signal line or as a message within the context of a communication protocol, to a control device of the X-ray device. The occurrence of a corresponding signal may be taken into account as the parameter of the radiation source. In the simplest case, the interference condition for a projection image may be fulfilled precisely when arcing has been identified during the recording of this projection image and a corresponding signal sent to the control device. Identification of arcing within the radiation source may be achieved by monitoring the impedance of the radiation source.

If identification of arcing by the radiation source itself is not provided or if this has to be validated, it is expedient, as explained below, for arcing to be identified in that the individual projection images and/or at least one other parameter of the radiation source are evaluated.

In the method, it is possible for a respective reference variable for the projection images to be calculated according to a predetermined calculation specification after which the fulfillment of the interference condition for the (respective) examined projection image depends upon a (respective) difference between the reference variable for this examined projection image and the reference variable for at least another one of the projection images. In this case, the interference condition may compare the difference with a limit value and the interference condition or a subcondition of the interference condition may be fulfilled if the difference exceeds the limit value. In this case, utilization may be made of the fact that certain reference variables of the projection images, which will be explained in more detail below, will probably only change insignificantly, in particular between projection images that are adjacent with respect to time and/or adjacent with respect to their recording angle. A significant deviation of a reference variable for a projection image from the corresponding reference variables for the adjacent projection image or images is indicative of interference to the recording of the projection image due to arcing.

The respective reference variable may depend upon a sum total of the image data for all the pixels or a subgroup of the pixels of the respective projection image and/or depend upon a sum total of variables derived for each of these pixels determined as a function of the image data of the respective pixel. Apart from a scaling factor, an evaluation of the sum total of all the pixels corresponds, for example, to a comparison of the average radiation intensities or attenuations for the projection images.

As explained in the introduction, arcing results in reduced radiation intensity during the recording of the respective projection image. Hence, a lower average value of the radiation intensities and hence of the sum total of the radiation intensities of the individual pixels is expected if arcing occurs. More complex relationships may result in both the case of an evaluation of the attenuation and in cases where the radiation intensity of the X-rays is controlled or regulated by a control device of the X-ray device.

If, for example, as explained in the introduction, attenuation is determined, this depends upon a ratio of the emitted radiation intensity and the acquired radiation intensity. If both these two variables are acquired correctly, in the case of a reduction in the emitted radiation intensity due to arcing, with a detector, this ratio remains substantially constant. However, a noise signal of a real detector may result in a much lower contrast. This may result in attenuations being underestimated. In this case, the summation may be restricted to the pixels for which large changes are expected, e.g., to pixels for which strong attenuation is expected.

Therefore, in the method, it is also possible for the sum total described to be calculated only from a subgroup of the pixels lying close to the center of the respective projection image. In particular, summation may be performed for a central rectangular region with a side length of for example several tens or several hundreds of pixels.

In order to take account of control or regulation of the radiation intensity, it is possible for corresponding control and/or regulating variables to be acquired after which the sum total and/or the image data of the individual pixels may be scaled as a function of these variables. It is also possible for the image data to be preprocessed before the summation, for example in that attenuations are determined from radiation intensities or vice versa.

Additionally, or alternatively to the image data, it is also possible for parameters of the radiation source to be evaluated. The parameters of the radiation source acquired may be an accelerating voltage and/or an operating current and/or a pulse duration and/or an emitted radiation intensity of the radiation source during the acquisition of the respective projection image. The emitted radiation intensity may, as already explained, be acquired by a separate radiation detector. It is also possible with certain pixels to assume that attenuation of the X-rays for these pixels did not occur in any of the projection images and thus the radiation intensity may also be determined from the projection images themselves.

In the simplest case, each parameter of the radiation source may be compared separately with a respective limit value in order to determine whether the interference condition or a subcondition of the interference condition is fulfilled. The individual subconditions of the interference condition may be logically linked so that the interference condition may be fulfilled if at least one of the subconditions is fulfilled, or may be fulfilled only if all the subconditions are fulfilled. Of course, more complex links are also possible.

The parameters of the radiation source may also be influenced by the fact that the radiation intensity of the radiation source is controlled or regulated, for example, in order to achieve a specific minimum contrast. Such control or regulation may be taken into account in the context of the evaluation of the parameters in that, for example, the parameters are scaled or provided with an offset before a comparison of limit values. It is also possible for the interference condition or a subcondition of the interference condition to be dependent upon an in particular weighted sum total of the parameters.

The fulfillment of the interference condition for the (respective) examined projection image may also be dependent on a difference between the parameter of the radiation source for recording the (respective) examined projection image and for recording at least another one of the projection images. In other words, it is possible for not only the values of the parameters to be taken into account during the recording of a respective examined projection image per se, but additionally or alternatively also the change to these parameters between individual projection images. This enables sudden jumps in parameter values to be identified. Then, the interference condition or a subcondition of the interference condition may be fulfilled if a corresponding difference exceeds a prespecified limit value for the difference. It is however also possible for example to evaluate weighted sum totals of the differences for different parameters.

The other projection image used to determine the difference between the parameters of the radiation source or to compare the reference variables or at least one of these other projection images may be a projection image adjacent to the (respective) examined projection image with respect to the recording angle and/or the recording time. An evaluation of temporally successive projection images, e.g., which are adjacent with respect to their recording time, makes it easy to identify jumps in the temporal course of the at least one parameter or the comparative value. On the other hand, projection images that were recorded at recording angles that are adjacent to one another may be particularly similar, thus making deviations due to arcing particularly easy to identify. If, as is frequently the case with computed tomography, the projection images are recorded such that projection images are acquired at adjacent recording angles at adjacent recording times, it is easy for both conditions to be fulfilled. In particular, the other projection images used may be at least one projection image recorded immediately before and one recorded immediately after the examined projection image with respect to the recording time and/or the recording angle.

As mentioned above, under some circumstances, it may be difficult in the method to differentiate between a break in the intensity of the X-rays due to arcing and due to automatic regulation of the intensity, for example in order to adjust an intensity as a function of properties of an examination object. It is therefore possible for at least one control parameter of an automated intensity control of the radiation source to be detected, wherein the fulfillment of the interference condition is dependent on the control parameter for the (respective) examined projection image. The control may be a regulation. This enables changes to the image data or the parameters of the radiation source expected due to the intensity control to be at least partially compensated during the evaluation of the interference condition, thus making it easier to identify changes to the corresponding variables due to arcing. If it is not possible to evaluate such control parameters of an automated intensity control used, the method may still be used in that sufficiently large limit values are used for changes to the parameters or the image data so that the interference condition is not triggered by normal intensity control interventions.

Following the above-explained identification of projection images with interference, it is possible to react to this interference in different ways in order to reduce artifacts in the three-dimensional image dataset. One possibility for this is that, first, as a function of all the projection images or exclusively the projection images with no interference, a three-dimensional auxiliary dataset is reconstructed after which a (respective) synthetic projection image that replaces the (respective) projection image with interference in the reconstruction of the image dataset is calculated from the auxiliary dataset. Hence, an iterative approach is used in which, first, a reconstruction is performed, the result of the reconstruction is used to provide the synthetic projection image, and is then reconstructed again. This iterative procedure may also be performed multiple times.

This procedure ultimately reduces the influence of the projection images with interference on the reconstructed image dataset, thus also enabling artifacts resulting from interference to the projection image to be reduced. If all the projection images are used for the reconstruction, the synthetic projection image is dependent upon the image data of the projection image with interference and upon at least parts of the image data of further projection images. If exclusively projection images for which the interference condition is not fulfilled are used for the reconstruction of the auxiliary dataset, the projection images with interference are disregarded during the determination of the image dataset.

In the method, in the context of the reconstruction of the image dataset or the auxiliary dataset, image data for the different projection images may be weighted differently, wherein the weighting of the image data of at least one of the projection images depends upon whether a projection image adjacent to this projection image with respect to the recording angle and/or the recording time is the projection image with interference or one of the projection images with interference. This may be advantageous if this projection image with interference is disregarded or given a lower weighting than the projection images with no interference during the determination of the image dataset. This approach to artifact reduction may be particularly simple to implement because, in many reconstruction methods, the individual projection images are already weighted differently, in particular, as a function of the recording image. An additional change to the weighting of projection images adjacent to projection images with interference or the projection images with interference themselves is simple to add.

In place of the (respective) projection image with interference, a (respective) synthetic projection image, which is calculated as a function of the image data of at least one projection image with no interference next adjacent to this projection image with interference with respect to the recording angle and/or the recording time may be used in the context of the reconstruction of the image dataset or the auxiliary dataset. In particular, the two next adjacent projection images with no interference, which are acquired before and after the projection image with interference, may be used to generate the synthetic projection image with respect to time or with respect to the recording angle. In particular, it is possible to calculate point-by-point a weighted sum total of the pixels of the projection images with no interference in order to generate the synthetic projection image. If the projection images with no interference are equidistant from the projection image with interference with respect to the recording angle or the recording time, it is possible to calculate the average value of the image data of the corresponding pixels in the projection images with no interference for every pixel. It is also possible to weight the pixels of the adjacent projection images with no interference as a function of how greatly the recording angle or the recording time of the respective projection image without interference differ(s) from the corresponding variables of the projection image with interference. The synthetic projection image may be considered to be an interpolation of the next adjacent projection images without interference that replaces the projection image with interference.

A corresponding interpolation may also be performed for individual pixels in the three-dimensional Radon space. Unlike the previous procedure, in which the interpolation is performed based on the projection images, with interpolation in the Radon space, depending upon the pixel to be replaced, pixels may be selected from different projection images or from a different position in the individual projection images in order to replace the image data or to be taken into account within the context of a weighted sum total that replaces the image data of the pixel. If corresponding sum totals are calculated, it is also possible for the weighting factors used for different pixels in the projection image with interference to differ from one another.

It is possible for a measure for the distance between two respective pixels of the different projection images to be prespecified that depends upon the respective position of the pixels in the respective projection images and upon the recording angles of the respective projection images, wherein, in the context of the reconstruction of the image dataset or the auxiliary dataset, instead of the image data of a respective to-be-replaced pixel of the projection image with interference or of the projection images with interference, a selected pixel or a weighted sum total of a plurality of selected pixels is used, wherein the selection of the selected pixels is performed such that they form part of projection images with no interference and that the measure for the distance to the to-be-replaced pixel under this condition is minimal. The measure may describe the distance between these pixels in the Radon space. Here, this may be a Euclidean measure with a prespecified weighting of the angle and the position of the pixel in the respective projection image. This measure may represent a measure of the similarity of the integration lines via which a differential attenuation is integrated for the individual points. For a calculation of this kind, it may be assumed that the integration line stands approximately perpendicular on the radiation detector. Alternatively, however, it is also possible to take account of the radiation geometry of the radiation source, for example if a radiation source with a fan beam and a flat detector is used.

If a plurality of selected pixels is used, these may be selected under the additional condition that at least one of these pixels forms part of a projection image without interference recorded before the projection image with interference with respect to the recording angle or the recording time and at least one of these pixels forms part of a projection image without interference recorded after the projection image with interference.

In addition to the method, the disclosure relates to an X-ray device with a radiation source and a radiation detector that may be moved by a movement device for setting a recording angle, and a control device by which the radiation source, the radiation detector and the movement device for the acquisition of projection images of an examination object may be controlled, wherein the control device is able to carry out the method.

The disclosure also relates to a computer program, which may be loaded directly into a memory of a control device of an X-ray device, wherein the program is configured to carry out the acts of the method when the program is executed in the control device of the X-ray device.

The disclosure additionally relates to an electronically readable data medium with electronically readable control information stored thereupon, which includes at least one computer program and is configured to carry out the method when the data medium is used in a control device of an X-ray device.

BRIEF DESCRIPTION OF THE DRAWINGS

Further advantages and details of the disclosure may be derived from the following exemplary embodiments and the associated drawings disclosed herein.

DETAILED DESCRIPTION

Figure 1:
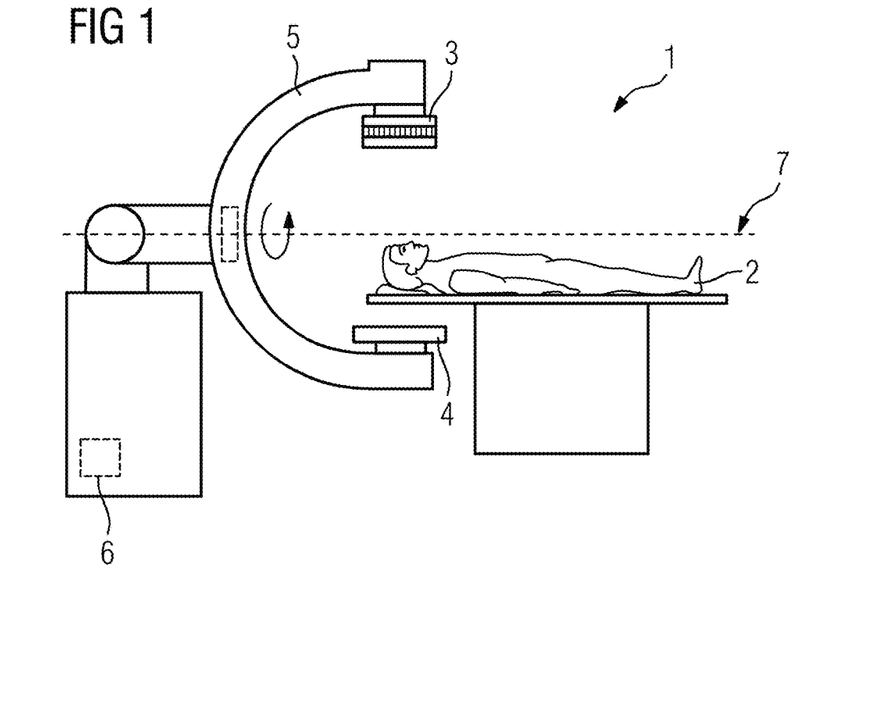
FIG. 1 depicts an exemplary embodiment of an X-ray device.

FIG. 1 depicts an X-ray device 1, which is able to record the projection images of an examination object 2 from a plurality of recording angles. To this end, a radiation source 3 and a radiation detector 4 are secured to a movement device 5, which is depicted as a C-arm in the example. Alternatively, the movement device 5 may be a gantry of a computed tomography scanner.

A control device 6 may control the movement device 5 in order to rotate the radiation source 3 and the radiation detector 4 about a central axis 7 and hence about the examination object 2 and hence to set different recording angles for the acquisition of projection images. Here, it is possible that with some of the projection images arcing may occur in the radiation source 3, in particular, in an X-ray tube of the radiation source. During this arcing, the intensity of the X-rays provided is reduced. This may result in underexposure and hence reduced contrast for the individual projection image.

If a corresponding projection image is used in the context of a reconstruction of a three-dimensional image dataset, with conventional reconstruction methods, this results in banding, which may greatly complicate the evaluation of the three-dimensional image data. Therefore, the control device 6 is configured to evaluate the image data of a respective projection image or at least one parameter of the radiation source during the recording of the respective projection image in order to identify projection images with interference, in which arcing has occurred. Subsequently, the reconstruction of the three-dimensional image dataset may take place such that the projection images with interference are disregarded during the determination of the three-dimensional image dataset or are given a lower weighting than all the projection images with no interference or are replaced by a synthetic projection image that is generated as a function of at least parts of the image data of the respective projection image with interference and at least another one of the projection images.

Different examples of the implementation of such a method performed by the control device 6 are described in the following with references to FIGS. 2 to 5, wherein FIG. 2 relates to the acquisition of the projection images and the identification of the projection images with interference and FIGS. 3 to 5 relate to different possibilities for the reconstruction of the three-dimensional image dataset.

Figure 2:
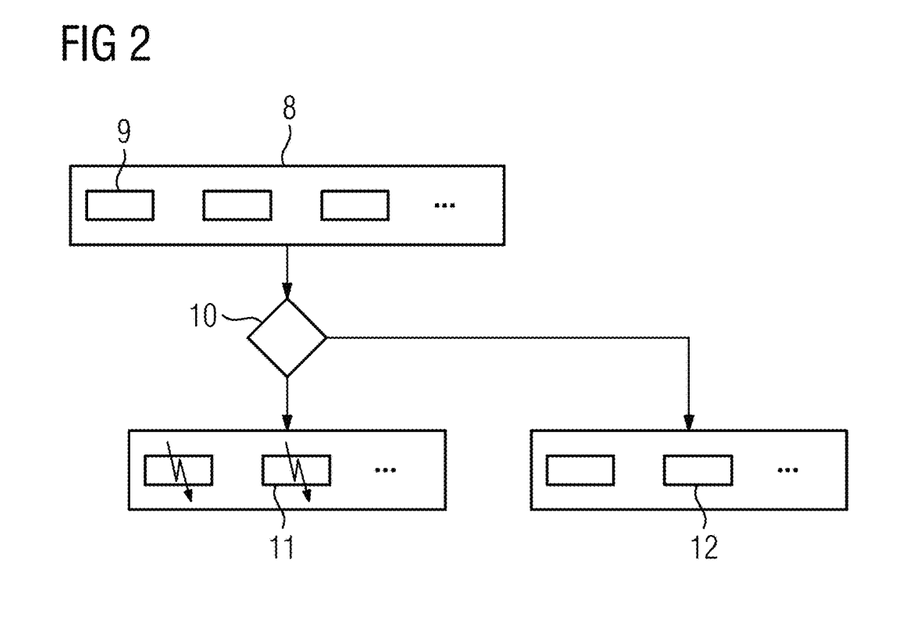
FIG. 2 depicts a flowchart for the acquisition of the projection images and for the identification of projection images with interference in an exemplary embodiment of the method.

As depicted in FIG. 2, in the processing block 8, a plurality of projection images 9 of the examination object 2 are recorded from a plurality of recording angles. To this end, the control device 6 in each case controls the movement device 5 in order to set the corresponding recording angle with respect to the central axis 7, after which the radiation source 3 is actuated to emit one or more X-ray pulses and the image data of the respective projection image 9 is acquired via the radiation detector 4, which is a pixel detector.

After the acquisition of the projection images 9, a check is performed in the processing block 10 for each of the projection images 9 as to whether in each case an interference condition is fulfilled. This interference condition evaluates, as explained in more detail below, at least parts of the image data of the respective examined projection image and/or at least one parameter of the radiation source during the recording of the respective examined projection image. The evaluation of the interference condition classifies the projection images 9, wherein the projection images 9 for which the interference condition is fulfilled are classified as projection images with interference 11 for which it is assumed that arcing occurred in the radiation source 3 during the acquisition of the respective projection image. The remaining projection images 9 are classified as projection images with no interference 12.

Identification of the projection images with interference 11 in the processing block 10 may take place in numerous ways. The identification methods explained in the following may in each case be used separately from one other or also combined with one another so that the interference condition may include a plurality of subconditions which are logically linked. It is for example also possible for some of the limit value comparisons explained in the following to be combined in that a weighted sum total is formed from individual variables that may be indicative of interference and the weighted sum total is compared with a common limit value.

An interference condition may be evaluated particularly simply if the radiation source 3 is itself configured such that it is able to identify arcing in the radiation source. For example, it is possible for voltages and currents used in the radiation source to generate the X-rays to be evaluated in order to detect an impedance of the radiation source or an X-ray tube used. If, for example, it is detected that a corresponding impedance or the real part of this impedance is below a certain limit value, this may be evaluated as indicative of arcing. Of course, it also possible to use other acquisition possibilities within the radiation source. For example, it is possible to detect light emission from the X-ray tube or the like. If a corresponding identification is made, the radiation source 3 may provide corresponding information to the control device 6 via a signal line, wherein the interference condition or a subcondition of the interference condition is fulfilled if a corresponding signal is present during the recording of the projection image.

Additionally, or alternatively, parameters of the radiation source, (e.g., an accelerating voltage, an operating current, a pulse duration, and/or an emitted radiation intensity), may be acquired and evaluated by the control device 6. Because these parameters may be dependent upon an automatic intensity regulation for the radiation intensity of the X-rays, it is expedient also to acquire at least one parameter of this intensity regulation and take it into account in the context of the evaluation of the interference condition. For example, limit values may be adjusted and/or the parameters of the radiation source may be scaled and/or provided with offsets.

In the simplest case, it is possible to evaluate exclusively the parameters of the radiation source for precisely the examined projection image in the context of the interference condition, e.g., to compare them for example with limit values. However, a more reliable identification of arcing may be possible if a difference is evaluated between the respective parameter of the radiation source for recording the respectively examined projection image and for recording at least another one of the projection images, which is in particular adjacent to the examined projection image with respect to the recording angle and/or the recording time. This enables the identification of jumps in the parameters of the radiation source that are indicative of arcing.

Additionally, or alternatively, it is possible to examine the image data of the examined projection image itself in each case. Here it is possible for directly acquired radiation intensities to be evaluated. However, attenuations determined from these radiation intensities may be identified. Corresponding attenuations may be calculated as the logarithm of the quotient of the radiation intensity emitted by the radiation source and the radiation intensity acquired in the respective pixel acquired. Corresponding attenuations are particularly simple to further process in the context of the reconstruction because they correspond to a line integral along the beam path of the X-rays via respective differential attenuations due to the examination object or due to other objects in the beam path.

If radiation intensities are evaluated, reduced emitted radiation intensity necessarily results in a reduction in the acquired radiation intensities for all the pixels of the respective projection image. Hence, the interference condition may be dependent upon an in particular weighted sum total of the acquired radiation intensities of all the pixels of the projection image or upon at least some of the pixels. This weighted sum total may be compared directly with a limit value, but a difference may be calculated from this sum total and a corresponding sum total, (e.g., a reference variable), of one or more adjacent projection images with respect to the recording angle or the recording time and compared with a limit value in order to identify jumps in the acquired intensity.

If attenuations are acquired, a reduction in the emitted radiation intensity due to arcing may not result in any change to the measurement data. However, in real X-ray devices, a reduction in the radiation intensity, in particular due to detector noise and/or a minimum sensitivity of the detector, would result in a reduction of the image contrast of the projection images. The outcome of this may be that attenuation is underestimated for greatly attenuated X-rays.

It is again possible to calculate a weighted sum total for all the pixels or at least some of the pixels of the examined projection image and evaluate this in the context of the interference condition. As explained above, direct comparison with a limit value is possible, but a difference from a corresponding sum total for adjacent projection images may be calculated.

With arcing, the acquired attenuations change, in particular, in those regions in which strong attenuation is expected, it is advantageous for such a sum total, in particular, exclusively to take account of those pixels at which strong attenuation is expected, for example, pixels in the center of the respective projection image.

In the case of automatic intensity regulation for the radiation source, it is also possible for the image data of the projection images to be influenced thereby and so, as explained with respect to the evaluation of the parameters of the radiation source, it is also expedient to take account of parameters of this automatic regulation in the evaluation of the image data in the context of the interference condition.

Following the identification of the projection images with interference explained with reference to FIG. 2, now the three-dimensional image dataset is reconstructed, wherein artifact formation due to the projection images with interference 11 is to be avoided as far as possible. Different possibilities for this are depicted in FIGS. 3 to 5.

Figure 3:
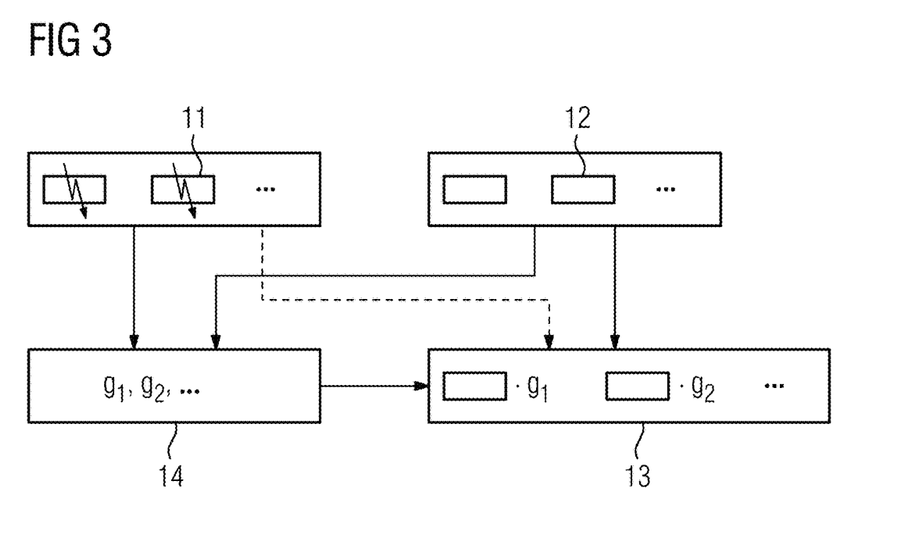
FIGS. 3 to 5 depict flowcharts for the reconstruction of a three-dimensional image dataset from the acquired projection images for different exemplary embodiments of the method.

In the exemplary embodiment depicted in FIG. 3, the reconstruction of the three-dimensional image dataset in the processing block 13 is performed exclusively as a function of the projection images with no interference 12, e.g., independently of the image data of the projection images with interference 11. In order to compensate for the fact that the projection images with interference 11 are disregarded in the reconstruction, the weighting factors $g_1$, $g_2$, etc., with which the image data of the projection images with no interference 12 are weighted in the reconstruction, are determined in the processing block 14 as a function of whether an adjacent projection image to the respective projection image with no interference 12 with respect to the recording angle or the recording time is a projection image with interference 11. Accordingly, it is possible to increase the weighting factors for the image data of the projection images with no interference 12 lying adjacent to projection images with interference 11 thus enabling the fact that the projection images with interference 11 are disregarded to be compensated to a large extent.

The described procedure is particularly easy to integrate in conventional reconstruction methods because these are frequently anyway provided with, in particular, recording-angle-dependent, weighting of the image data of individual projection images. As described above, it is easy to modify this procedure.

Of course, it is also possible for the projection images with interference to be not completely disregarded in the reconstruction but only to reduce the weighting factors assigned thereto compared to the weighting factors of the projection images with no interference.

Figure 4:
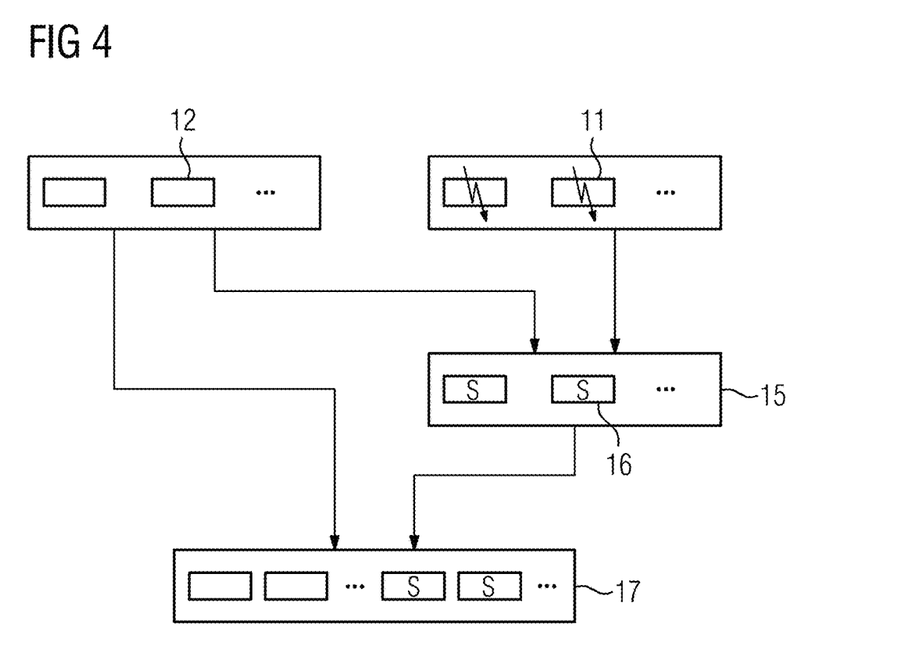

FIG. 4 depicts an alternative approach for the reconstruction of the three-dimensional image data. In this case, all the projection images with interference 11 are replaced in the processing block 15 by synthetic projection images 16. The synthetic projection images 16 may be generated completely independently of the projection images with interference 11 in that image data for the individual pixels of the synthetic projection images 16 is in each case calculated from image data of adjacent projection images without interference 12 with respect to time or the recording angle to the respective projection image with interference.

If both projection images adjacent to a projection image with interference 11 are projection images with no interference 12, it is possible to calculate for each pixel of the synthetic projection image 16 an average of the image data of the corresponding pixels of the adjacent projection images with no interference. If it is determined for a plurality of adjacent projection images that these are projection images with interference 11, it is also possible for a projection image with interference 11 that is to be replaced by a synthetic projection image 16 to have different distances from the next adjacent projection images with no interference 12 with respect to the recording angle or the recording time. This may be taken into account by the fact that the pixels of the synthetic projection image 16 are calculated as a weighted sum total of the corresponding image data of the adjacent projection images with no interference 12, wherein the weighting of the individual projection images is in particular inversely proportional to the temporal interval or to the angular distance.

The reconstruction of the three-dimensional image data in the processing block 17 may be performed in the conventional way in the prior art, wherein, however, a respective synthetic projection image 16 is used instead of the projection image with interference 11.

In one variant of the procedure described with respect to FIG. 4, it would also be possible for the individual synthetic projection images 16 to be calculated not completely independently of the respective projection image with interference 11 but for the image data of the corresponding projection image 11 also to be taken into account, for example in the context of a weighted sum total for the individual pixels of the synthetic projection image 16.

In the method explained with reference to FIG. 4, the individual pixels of the synthetic projection images 16 are calculated on the basis of adjacent projection images without interference 12. In some cases, the quality of the reconstruction may be further improved if, instead of this, interpolation in the Radon space is performed. The image data of the individual projection images or attenuation calculated therefrom for the individual pixels may be treated as pixels in a three-dimensional Radon space from which a Radon transform of the three-dimensional image dataset is determined. Pixels in the three-dimensional Radon space assigned to projection images with interference 11 may be replaced by synthetic pixels interpolated from adjacent pixels in the Radon space. In other words, for each pixel of a projection image with interference 11, it is possible to calculate at least one adjacent pixel in the Radon space, which forms part of to a projection image with no interference 12 and is the closest adjacent pixel to the pixel to be replaced. To this end, it is possible to specify a measure for the distance between two respective pixels of the different projection images that is dependent upon the respective position of the pixels in the respective projection images and upon the recording angles of the respective projection images. Then, at least one selected pixel is selected that forms a closest adjacent pixel to the pixel to be replaced with respect to this measure and which is assigned to a projection image with no interference 12. Of course, it is also possible for a plurality of selected pixels to be determined and for the image data of the pixel to be replaced to be calculated as the weighted sum total of the image data of these selected pixels.

Figure 5:
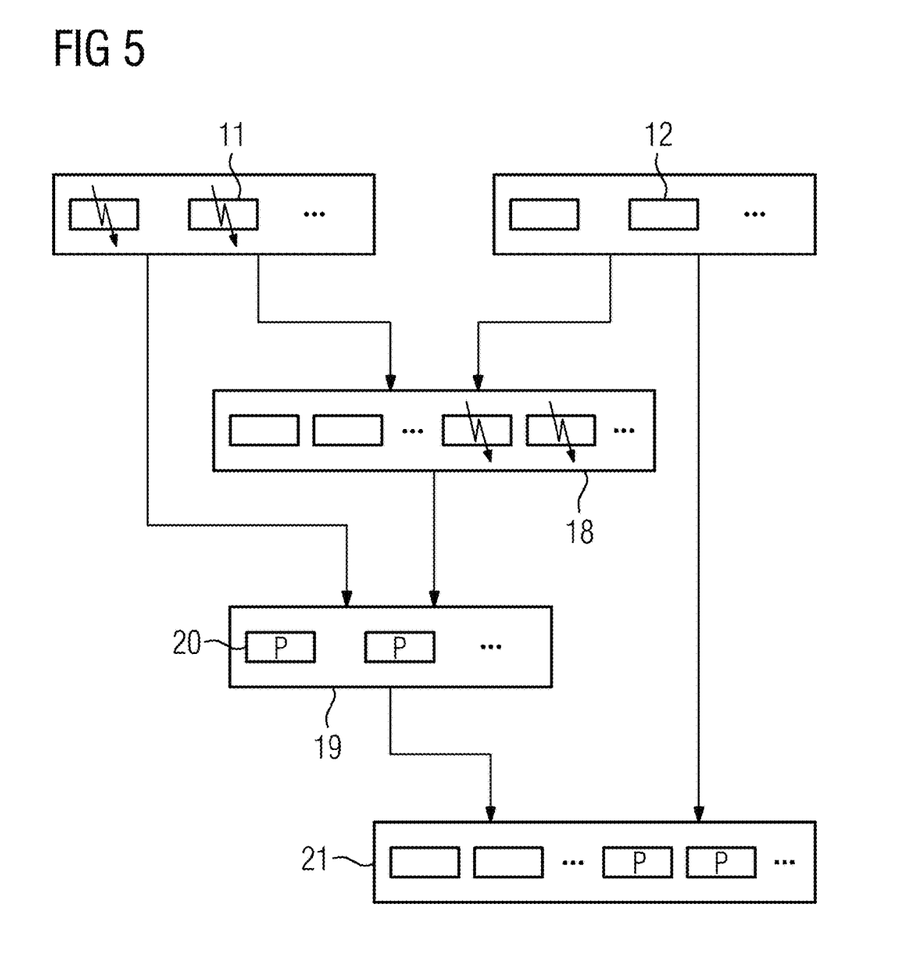

FIG. 5 depicts a further variant for reducing artifacts due to the projection images with interference 11 in the reconstructed three-dimensional image data. In this case, an iterative method is used with which, first, an auxiliary dataset is reconstructed in the processing block 18. In this case, the reconstruction is performed as is conventional in the prior art as a function of both the projection images with no interference 12 and the projection images with interference 11. In the processing block 19, a synthetic projection image 20 is determined from this auxiliary dataset for each of the projection images with interference 11 in that a projection of the auxiliary dataset is performed according to the recording geometry of the corresponding projection image with interference 11. This results in synthetic projection images that are dependent upon both the projection image with interference 11 and further projection images with no interference 12. The final reconstruction of the three-dimensional image dataset in processing block 21 is performed as a function of both the projection images with no interference 12 and the synthetic projection images 20. Hence, the replacement of the projection images with interference 11 by the synthetic projection images 20 reduces the dependence of this three-dimensional image dataset upon the projection images with interference 11.

A further improvement in the quality of the resulting three-dimensional image data with the iterative procedure described may potentially be achieved in that the reconstruction of the auxiliary dataset is performed in the processing block 18 independently of the projection images with interference 11. For example, the reconstruction of the auxiliary dataset may be performed in the processing block 18 as explained for the processing blocks 13 or 17 in FIGS. 3 and 4 with respect to the image dataset.

Figure 6:
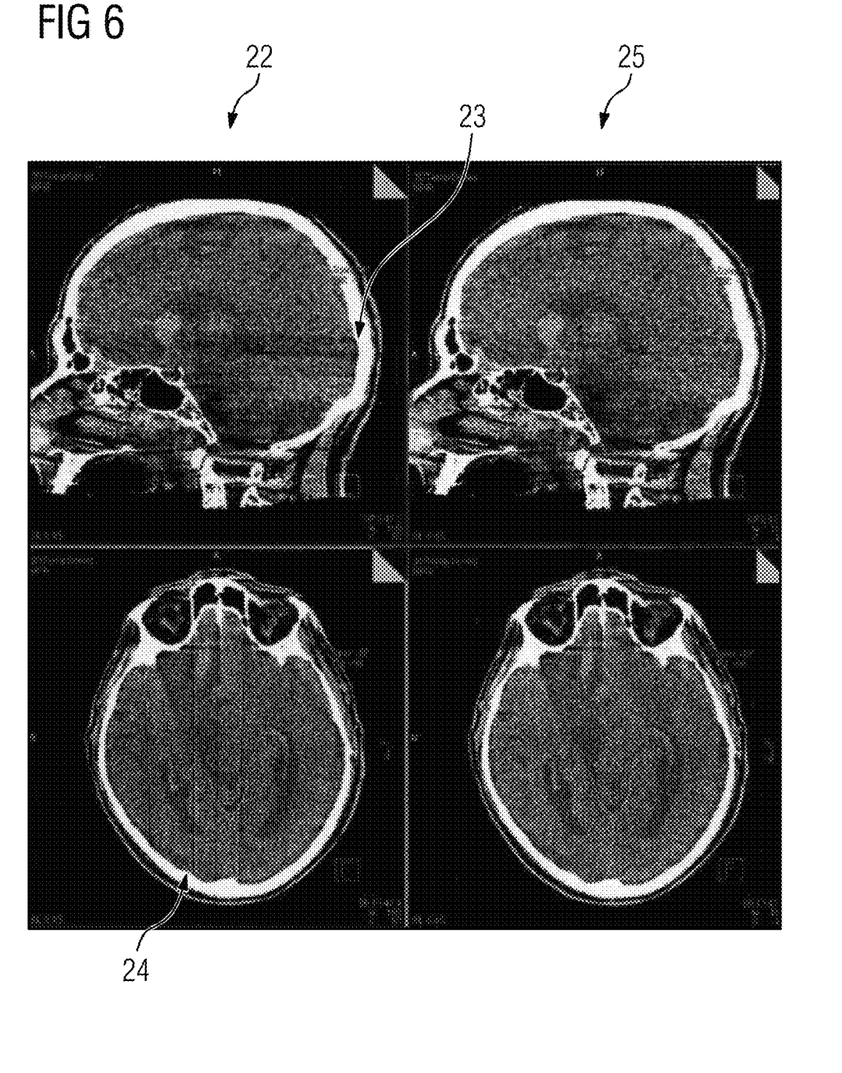
FIG. 6 depicts a comparison of reconstruction results for an exemplary embodiment of the method, and a reconstruction method according to the prior art.

FIG. 6 depicts an example of the application of an exemplary embodiment of the method described with real measurement data. The left column 22 shows an axial and sagittal slice of a three-dimensional image reconstructed according to a conventional method dataset. In the context of this acquisition, arcing occurred several times resulting in a plurality of bands in the images, of which bands 23 and 24 are shown by way of example.

In the right column 25, this banding is clearly reduced. To achieve this, reconstruction was used, in which the projection images with interference are disregarded during the determination of the three-dimensional image dataset. In this case, the approach explained with respect to FIG. 4 was used, in which projection images with interference 11 are replaced by synthetic projection images 16 interpolated from the projection images with no interference 12. In addition, to improve the quality of the three-dimensional image dataset further, an iterative method was used as explained with respect to FIG. 5. In this case, the auxiliary dataset in the processing block 18 was determined as a function of the projection images with no interference 12 and the synthetic projection images 16 determined as explained above. This auxiliary dataset was used to determine further synthetic projection images 20 that replace the projection images with interference 11 in the context of the final reconstruction.

The method described herein may also be provided in the form of a computer program that implements at least one respective method on the control device 6 when it is executed on the control device 14. It is also possible for an electronically readable data medium to be provided (not shown) with electronically readable control information stored thereupon including at least one computer program as described and being embodied to carry out a method as described when the data medium is used in a control device 6 of an X-ray device 1.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a three-dimensional image dataset by an X-ray device, the method comprising:
   recording projection images of an examination object from a plurality of recording angles, wherein image data of the projection images describe acquired radiation intensities or attenuations determined therefrom of X-rays emitted by a radiation source of the X-ray device for a plurality of pixels;
   evaluating the recorded projection images for a presence of an interference condition, wherein the interference condition is dependent upon at least one parameter of the radiation source during the recording of the respective projection image, wherein the at least one parameter indicates that the respective examined projection image is a projection image with interference during the recording of which arcing has occurred in the radiation source;
   identifying an interference within at least one recorded projection image of the recorded projection images; and
   reconstructing the three-dimensional image data set from the recorded projection images, wherein in the reconstruction:
      the at least one identified projection image with interference is disregarded, or
      the at least one identified projection image with interference is given a lower weighting than each projection image with no interference for which an interference condition is not fulfilled, or
      the at least one identified projection image with interference is replaced by a respective synthetic projection image generated as a function of at least parts of the image data of the respective projection image with interference and at least one additional projection image.

2. The method of claim 1, wherein a respective reference variable is calculated for the projection images according to a predetermined calculation specification after which fulfillment of the interference condition for the respective projection image depends upon a respective difference between the reference variable for the respective projection image and the reference variable for at least an additional projection image.

3. The method of claim 2, wherein the additional projection image used is a projection image adjacent to the respective projection image with respect to the recording angle and/or the recording time.

4. The method of claim 2, wherein the respective reference variable depends upon a sum total of the image data for all the pixels or a subgroup of the pixels of the respective projection image and/or depends upon a sum total of variables derived for each pixel determined as a function of the image data of the respective pixel.

5. The method of claim 4, wherein the additional projection image used is a projection image adjacent to the respective projection image with respect to the recording angle and/or the recording time.

6. The method of claim 1, wherein the parameter of the radiation source is one or more of an accelerating voltage, an operating current, a pulse duration, or an emitted radiation intensity of the radiation source during the acquisition of the respective projection image.

7. The method of claim 6, wherein fulfillment of the interference condition for the respective examined projection image is dependent on a difference between the parameter of the radiation source for recording the respective projection image and for recording at least an additional projection image.

8. The method of claim 7, wherein the additional projection image used is a projection image adjacent to the respective projection image with respect to the recording angle and/or the recording time.

9. The method of claim 1, wherein at least one control parameter of an automated intensity control of the radiation source is detected, and
wherein fulfillment of the interference condition is dependent on the control parameter for the respective examined projection image.

10. The method of claim 1, further comprising:
reconstructing a three-dimensional auxiliary dataset as a function of all the projection images or exclusively the projection images with no interference; and
calculating, from the auxiliary dataset, a respective synthetic projection image that replaces the respective projection image with interference in the reconstruction of the image dataset.

11. The method of claim 10, wherein, in the reconstruction of the image dataset or the auxiliary dataset, image data for the different projection images is weighted differently,
wherein the weighting of the image data of at least one of the projection images depends upon whether a projection image adjacent to this projection image with respect to the recording angle and/or the recording time is a projection image with interference.

12. The method of claim 10, wherein, in the reconstruction of the image dataset or the auxiliary dataset, a synthetic projection image is calculated in place of the respective projection image with interference as a function of the image data of at least one projection image with no interference adjacent to the projection image with interference with respect to the recording angle and/or the recording time.

13. The method of claim 10, wherein a measure for the respective distance between two respective pixels of the different projection images is prespecified that depends upon the respective position of the pixels in the respective projection images and upon the recording angles of the respective projection images,
wherein, in the reconstruction of the image dataset or the auxiliary dataset, a selected pixel or a weighted sum total of a plurality of selected pixels is used instead of the image data of a respective to-be-replaced pixel of the at least one projection image with interference, and
wherein the selection is performed such that the selected pixels form part of projection images with no interference and that the measure for the distance to the to-be-replaced pixel is minimal.

14. The method of claim 1, wherein, in the reconstruction of the image dataset, image data for the different projection images is weighted differently,
wherein the weighting of the image data of at least one of the projection images depends upon whether a projection image adjacent to this projection image with respect to the recording angle and/or the recording time is a projection image with interference.

15. The method of claim 1, wherein, in the reconstruction of the image dataset, a synthetic projection image is calculated in place of the respective projection image with interference as a function of the image data of at least one projection image with no interference adjacent to the projection image with interference with respect to the recording angle and/or the recording time.

16. The method of claim 1, wherein a measure for the respective distance between two respective pixels of the different projection images is prespecified that depends upon the respective position of the pixels in the respective projection images and upon the recording angles of the respective projection images,
wherein, in the reconstruction of the image dataset, a selected pixel or a weighted sum total of a plurality of selected pixels is used instead of the image data of a respective to-be-replaced pixel of the at least one projection image with interference, and
wherein the selection is performed such that the selected pixels form part of projection images with no interference and that the measure for the distance to the to-be-replaced pixel is minimal.

17. An X-ray device comprising:
a movement device;
a radiation source;
a radiation detector configured to be moved by the movement device for setting a recording angle; and
a control device by which the radiation source, the radiation detector, and the movement device are configured to be controlled for the acquisition of projection images of an examination object, wherein the control device is configured to:
record projection images of the examination object from a plurality of recording angles, wherein image data of the projection images describe acquired radiation intensities or attenuations determined therefrom of X-rays emitted by a radiation source of the X-ray device for a plurality of pixels;
evaluate the recorded projection images for a presence of an interference condition, wherein the interference condition is dependent upon at least one parameter of the radiation source during the recording of the respective projection image, wherein the at least one parameter indicates that the respective examined projection image is a projection image with interference during the recording of which arcing has occurred in the radiation source;
identify an interference within at least one recorded projection image of the recorded projection images; and
reconstruct the three-dimensional image data set from the recorded projection images, wherein in the reconstruction:
the at least one identified projection image with interference is disregarded, or
the at least one identified projection image with interference is given a lower weighting than each projection image with no interference for which an interference condition is not fulfilled, or
the at least one identified projection image with interference is replaced by a respective synthetic projection image generated as a function of at least parts of the image data of the respective projection image with interference and at least one additional projection image.

18. An electronically readable data medium with electronically readable control information stored thereupon, which comprises at least one computer program and is, when the data medium is used in a control device of an X-ray device, configured to:
record projection images of the examination object from a plurality of recording angles, wherein image data of the projection images describe acquired radiation intensities or attenuations determined therefrom of X-rays emitted by a radiation source of the X-ray device for a plurality of pixels;
evaluate the recorded projection images for a presence of an interference condition, wherein the interference condition is dependent upon at least one parameter of the radiation source during the recording of the respective projection image, wherein the at least one parameter indicates that the respective examined projection image is a projection image with interference during the recording of which arcing has occurred in the radiation source;

identify an interference within at least one recorded projection image of the recorded projection images; and reconstruct the three-dimensional image data set from the recorded projection images, wherein in the reconstruction:

the at least one identified projection image with interference is disregarded, or the at least one identified projection image with interference is given a lower weighting than each projection image with no interference for which an interference condition is not fulfilled, or the at least one identified projection image with interference is replaced by a respective synthetic projection image generated as a function of at least parts of the image data of the respective projection image with interference and at least one additional projection image.

\* \* \* \* \*